United States Patent [19]
Boaz et al.

[11] Patent Number: 6,143,935
[45] Date of Patent: Nov. 7, 2000

[54] PROCESS FOR THE PREPARATION OF 1,3-DICARBONYL COMPOUNDS

[75] Inventors: Neil W. Boaz, Kingsport, Tenn.; M. Todd Coleman, Batesville, Ak.

[73] Assignee: Eastman Chemical Company, Kingsport, Tenn.

[21] Appl. No.: 09/088,775

[22] Filed: Jun. 2, 1998

Related U.S. Application Data

[60] Provisional application No. 60/048,398, Jun. 3, 1997.

[51] Int. Cl.[7] .................................................. C07C 45/45
[52] U.S. Cl. ........................ 568/314; 568/315; 568/346; 568/347; 568/388; 568/391
[58] Field of Search .................................... 568/314, 315, 568/316, 319, 327, 329, 331, 335, 346, 347, 348, 367, 368, 374, 388, 391, 397, 403, 407, 419

[56] References Cited

U.S. PATENT DOCUMENTS

| | | | |
|---|---|---|---|
| 3,845,133 | 10/1974 | Cohen | 260/586 |
| 4,175,012 | 11/1979 | MacKay et al. | 204/108 |
| 5,344,992 | 9/1994 | Drewes | 568/314 |
| 5,618,982 | 4/1997 | Gilbert | 568/346 |

FOREIGN PATENT DOCUMENTS

| | | |
|---|---|---|
| 714 046 | 9/1968 | Belgium . |
| 0 454 624 | 10/1991 | European Pat. Off. . |
| 0 470 856 | 2/1992 | European Pat. Off. . |
| 0 697 390 | 2/1996 | European Pat. Off. . |
| 224 589 | 7/1910 | Germany . |
| 1 618 442 | 12/1970 | Germany . |
| 95/00476 | 1/1995 | WIPO . |
| 95/24372 | 9/1995 | WIPO . |
| 97/28122 | 8/1997 | WIPO . |

OTHER PUBLICATIONS

Spitzmiller, Erwin R., "2–Thio–6–cyclopropyl–uracil", *J. Am. Chem. Soc.*, vol. 69, p. 2073 (1947).

Bloomfield, J.J., "Acylation of Ketones in Dimethyl Sulfoxide", *J. Org. Chem.*, 27:2742–2746 (1962).

Anselme, J.P., "A Convenient and Practical Preparation of Dibenzoylmethane", *J. Org. Chem.*, 32:3716–3718 (1967).

Hauser et al., "The Acylation of Ketones to Form β–Diketones or β–Keto Aldehydes", *Organic Reactions*, vol. 8, Chapter 3, pp. 59–196, John Wiley & Sons (1954).

Coombes et al., "On the Synthesis of 2–methylchromene–4–thione and 2–methyl–1–thiochromone", *Phosphorous and Sulfur*, vol. 14, No. 2, pp. 139–142 (1983).

Reid et al., "Addition of nitroalkanes to ortho–halo–nitrobenzenes. A new synthesis of 4–chloro–7–(trifluoromethyl)quinoline", *Tetrahedron Letters*, vol. 31, No. 8, pp. 1093–1096 (1990).

March, Jerry, "Advanced Organic Chemistry", John Wiley & Sons, Eds. New York, pp. 886–887 (1992).

Barlett, et al., "A Mild, Oxidative Nitro–to Carbonyl Conversion and a New Prostaglandin Synthon", *Tetrahedron Letter*, No. 4, pp. 331–334 (1977).

*Primary Examiner*—Sreeni Padmanabhan
*Attorney, Agent, or Firm*—Mike Blake; Harry J. Gwinnell

[57] ABSTRACT

The condensation reaction of a ketone with either an ester or a carbonate to form, respectively, a 1,3-diketone or a β-ketoester often affords poor results under the standard condensation reaction conditions. High yields and high purities of the desired product can be obtained by performing the reaction using an alkoxide base in DMSO as the sole solvent.

21 Claims, No Drawings

PROCESS FOR THE PREPARATION OF 1,3-DICARBONYL COMPOUNDS

This application claims under 35 U.S.C. § 119(e) the benefit of U.S. Provisional Application No. 60/048,398, filed Jun. 3, 1997, which is incorporated in its entirety by reference.

BACKGROUND OF THE INVENTION

1. Field of the Invention

The invention relates to a process for the preparation of 1,3-dicarbonyl compounds. The process involves a condensation reaction of a ketone with either an ester or a carbonate to form, respectively, a 1,3-diketone or a β-ketoester. Such 1,3-dicarbonyl compounds may be used as starting materials or intermediates for the synthesis of heterocycles, costabilizers for chlorinated polymers (e.g. polyvinyl chloride), or waste extractants (U.S. Pat. No. 4,175,012).

2. Description of the Related Art

Condensation reactions between ketones and esters are powerful methods for the preparation of 1,3-diketones, which are important synthetic intermediates for a variety of industrially important compounds such as herbicides. Several such compounds are isoxazole and derivatives thereof (Casado et al., WO 95/00476; and Cain et al., EP 470856). Though less reactive, a carbonate may be used in place of an ester to form a β-ketoester by a condensation reaction. These condensations, generally known as Claisen condensations, are usually performed under basic conditions. In many cases, the reaction is facile, and can be effected using an alkoxide base. However, when the ester is hindered or a relatively unreactive carbonate is used, the reaction is much more challenging and offers poor yields.

The Claisen condensation is a well-known reaction, and there are many methods to affect this condensation reaction. (Hauser et al., *Organic Reactions* 8:59 (1954)). The standard conditions under which 1,3-dicarbonyl compounds can be generally prepared include the use of an alkoxide base in a standard organic solvent such as an alcohol, an aromatic hydrocarbon, or an ether. These conditions are quite sufficient when the electrophile is either a formate, an acetate or another highly reactive ester. However, when the ester becomes more hindered, such as, for example, an isobutyrate, or when a less-reactive carbonate is used, these reaction conditions often fail. In these cases, the desired reaction can sometimes still be affected using an alkoxide by conducting the reaction in a high-boiling solvent such as toluene or xylene at high temperature, often with continuous removal of the generated alcohol. (Hauser et al., *Organic Reactions* 8:59 (1954); Reuther et al., EP 697,390). Claisen condensations can also be very sensitive to the order of addition of the reactants or may require a precise product isolation protocol in order to obtain the optimal product yield. (Krbechek et al., WO 95/24372).

Bases such as sodium hydride, sodium amide, and sodium tert-butoxide in an ethereal solvent, which irreversibly form the enolate anion of the ketone, have been used to promote conversion of reactants to the desired product. (Hauser et al., *Organic Reactions* 8:59 (1954); Drewes et al., EP 454,624). The anion of dimethyl sulfoxide, generated from DMSO and sodium hydride, has also been used to perform the Claisen condensation. (Bloomfield, J. J., *J. Org. Chem.* 27:2742 (1962); Anselme, J. P., *J. Org. Chem.* 32:3716 (1967)). However, sodium hydride is an expensive and dangerously reactive chemical, as it can vigorously release hydrogen upon reaction with an acidic material, even moist air. The use of a more innocuous and less expensive base, sodium methoxide, in a mixture of DMSO and an inert organic solvent has also been described. (Drewes et al., U.S. Pat. No. 5,344,992).

However, the use of standard Claisen condensation conditions to prepare 1,3-dicarbonyl compounds can suffer from poor yields and numerous by-products, which complicate isolation of the desired product. Accordingly, there still exists a need in the art for a straightforward and efficient process for the preparation of 1,3-dicarbonyl compounds upon condensation of a ketone with either an ester or a carbonate. The reaction should be insensitive to addition order, provide good yields, and not require a precise product isolation protocol. The 1,3-dicarbonyl compound should be produced in high yield and high purity.

SUMMARY OF THE INVENTION

This invention answers those needs and provides a high-yielding, straighiforward, efficient, and cost-effective process for the preparation of 1,3-dicarbonyl compounds by its use of an innocuous alkoxide base in DMSO as the sole solvent which affords improved results compared to other organic solvents alone or mixed with DMSO.

The invention provides a straightforward, efficient and cost-effective process for the preparation of 1,3-dicarbonyl compounds by reacting a ketone having an acidic proton at the α-position with an ester of formula (I):

(I)

in DMSO and the presence of an alkoxide base. The invention also provides a straightforward, efficient and cost-effective process for the preparation of 1,3-dicarbonyl compounds by reacting a ketone having an acidic proton at the 1c-position with a carbonate of formula (II):

(II)

in DMSO and in the presence of an alkoxide base.

DETAILED DESCRIPTION OF THE INVENTION

One embodiment of the invention is a process for the preparation of a 1,3-dicarbonyl compound by reacting, a ketone and an ester. The process reacts a ketone with an ester in a single step Claisen condensation. The reaction is carried out in the presence of an alkoxide base and DMSO as the sole solvent. This process, along with preferred embodiments, is described in more detail in the discussion and examples below.

The ketone may be any ketone which has an acidic proton at the a-position. Examples of suitable ketones include, but are not limited to, dialkyl ketones, alkyl aryl ketones, alkyl heteroaryl ketones, alkyl cycloalkyl, and alkyl heterocycloalkyl ketones. Unless indicated otherwise, an alkyl group as used throughout refers to a substituted or unsubstituted straight chain or branched hydrocarbon group. Preferably the alkyl group is a $C_1$–$C_{10}$ alkyl group, more preferably a primary alkyl group. A cycloalkyl group as used throughout refers to a substituted or unsubstituted cyclic hydrocarbon group. Preferably, the cycloalkyl group is a $C_3$–$C_8$ cycloalkyl group. Suitable examples of the cycloalkyl group include, but are not limited to, cyclopropyl, cyclopentyl, and cyclohexyl. A heterocycloalkyl group as used throughout refers to a substituted or unsubstituted cyclic hydrocarbon group containing at least one heteroatom. Preferably, the heterocycloalkyl group is a substituted or unsubstituted $C_3$–$C_7$ heterocycloalkyl group. Suitable examples of the heterocycloalkyl group include, but are not limited to, an imidazolidinyl, pyrazolidinyl, piperidinyl, piperazinyl, or morpholinyl group. An aryl group as used throughout refers to a substituted or unsubstituted aromatic group while a heteroaryl group as used throughout refers to a substituted or unsubstituted aromatic group containing at least one heteroatom. Possible heteroatoms for the heterocycloalkyl or heteroaromatic groups include nitrogen, oxygen, and sulfur. Preferred aryl or aromatic groups and heteroaryl or heteroaromatic groups include, but are not limited to, phenyl, furanyl, pyrrolyl, isopyrrolyl, thienyl, napthyl, pyridinyl, and pyranyl. Possible substituents include, but are not limited to, alkyl, aryl, heteroaryl, ether, thioether, halo, and other similar groups. Preferably, the ketone is a methyl ketone such as, for example, acetophenone, 2-thiomethyl-4-trifluoromethyl-acetophenone, cyclopropyl methyl ketone, or 3,3-dimethyl-2-butanone.

The ester may be any ester of formula (I):

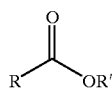

(I)

where R and R' are, independently, a substituted or unsubstituted $C_1$–$C_{10}$ alkyl group, a $C_3$–$C_8$ cycloalkyl group, a $C_3$–$C_7$ heterocycloalkyl group, or an aryl or heteroaryl group. Possible substituents include those as defined above. Preferably, R and R' are, independently, a $C_1$–$C_5$ alkyl or $C_3$–$C_6$ cycloalkyl group. More preferably, R and R' are, independently, for example, a methyl, ethyl, propyl or cyclopropyl group. Examples of suitable esters include, but are not limited to, methyl cyclopropanecarboxylate and methyl acetate. Preferably about 0.8–6 equivalents, more preferably about 2–3 equivalents, of ester based on the amount of ketone, is used upon reaction with the ketone.

The alkoxide base may be any alkoxide base capable of deprotonating an acidic proton at the a-position of the ketone as described above. Preferably, the alkoxide base is an alkali metal alkoxide or an ammonium alkoxide. The alkali metal of an alkali metal alkoxide may be any alkali metal including, for example, sodium, potassium, cesium and the like. Preferably, the alkali metal is sodium or potassium. More preferably, the alkali metal is sodium. The alkoxide of the alkoxide base may be derived from a lower alcohol, preferably from a $C_1$–$C_6$ alcohol, more preferably from a $C_1$–$C_4$ alcohol. Examples of suitable alkoxides include, but are not limited to, methoxides, ethoxides, t-butyl oxides and t-pentoxides. Examples of preferred alkoxide bases include, but are not limited to, sodium methoxide, sodium ethoxide, sodium t-pentoxide, potassium methoxide, potassium ethoxide, potassium t-butoxide, and ammonium t-butoxide. Preferably, the alkoxide base is sodium methoxide. The amount of alkoxide base required to effect the reaction is optimally about 1.5–3 equivalents, preferably about 2 equivalents, based on the amount of ketone. In a preferred embodiment, the alkoxide base is utilized in dry powder form rather than as an alcohol solution.

In order to achieve high yields and high purity of the condensation products, dimethyl sulfoxide (DMSO) is used as the sole solvent. By using DMSO as the sole solvent, improvements in yield of greater than about 10% are realized compared to the use of other inert organic solvents alone or mixed with DMSO. Although the amount of DMSO present in the reaction is not crucial for success of the reaction, for convenience sake, the amount of DMSO used is such that the concentration of the starting ketone is between about 1–2 M. The reaction may be conducted in DMSO at temperatures ranging from ambient temperature to about 90° C., preferably at temperatures ranging from about 40–55° C.

Another embodiment of the invention is a process for the preparation of a 1,3-dicarbonyl compound by reacting a ketone and a carbonate. The process reacts a ketone with a carbonate in a single step Claisen condensation. The reaction is carried out in the presence of an alkoxide base and DMSO as the sole solvent. This process, along with preferred embodiments, is described in more detail in the discussion and examples below.

The ketone is as described above. The carbonate may be any carbonate of formula (II):

(II)

where R" and R'" are, independently, a substituted or unsubstituted $C_1$–$C_{10}$ alkyl group, a $C_3$–$C_8$ cycloalkyl group, a $C_3$–$C_7$ heterocycloalkyl group, or an aromatic or heteroaromatic group. Suitable substituents include those as defined above. If R" or R'" are aromatic or heteroaromatic groups, the substituent may not be a nitro group. Preferably, R" and R'" are, independently, a $C_1$–$C_5$ alkyl group such as, for example, a methyl, ethyl, or propyl group. More preferably, R" and R'" are each a methyl group. In a preferred embodiment, an excess amount of carbonate is used upon reaction with the ketone. Preferably, about 1.5–6 equivalents of carbonate is used, more preferably about 2–3 equivalents, based on the amount of ketone.

For the process of preparing a 1,3-dicarbonyl compound by reacting a ketone and a carbonate, the alkoxide base is as described above. According to the invention, reaction between a ketone and a carbonate may be conducted in DMSO at temperatures ranging from ambient temperature to about 90° C., preferably at temperatures of about 40–55° C. Under such reaction conditions, yields of $\geq 69\%$ can be achieved.

Unlike work done previously, both embodiments of the invention are insensitive to the order of addition of the reactants and do not require a precise product isolation protocol in order to obtain the optimal product yield. Preferably, however, all reagents are mixed together at the start of the reaction.

A further understanding can be obtained by reference to certain specific examples which are provided herein for purpose of illustration only and are not intended to be limiting unless otherwise specified.

EXAMPLES

For the examples below which relate to the reaction between an aromatic ketone, 2-thiomethyl-4-trifluoromethylacetophenone, and an ester, methyl cyclopropanecarboxylate (MCPC).

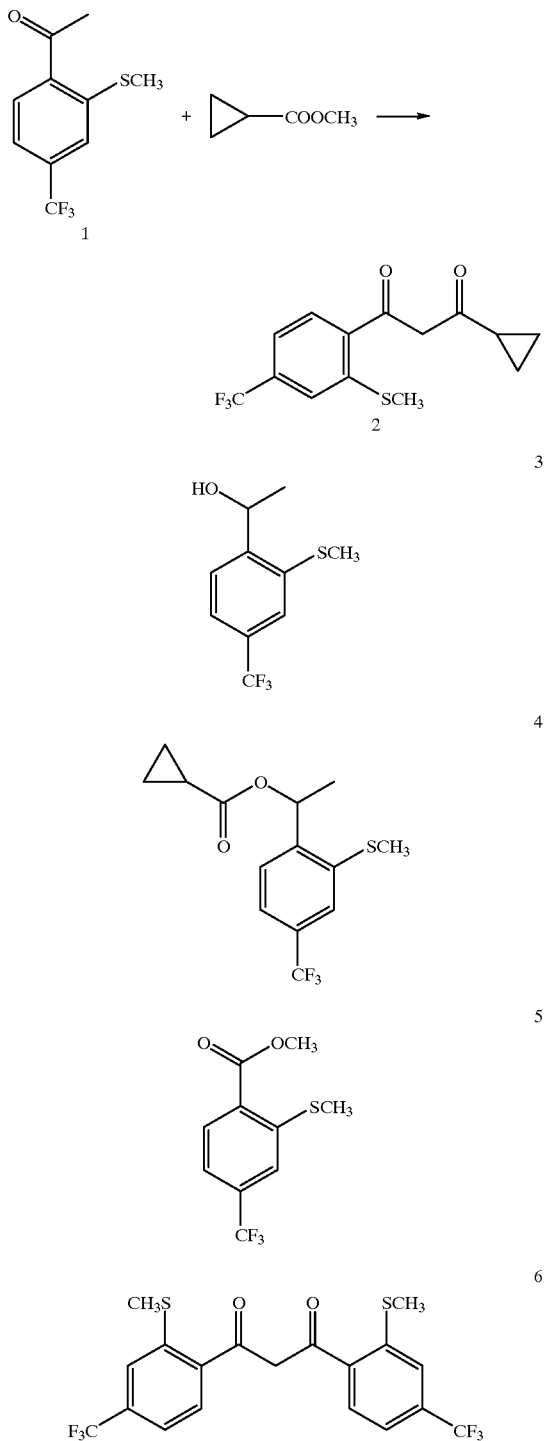

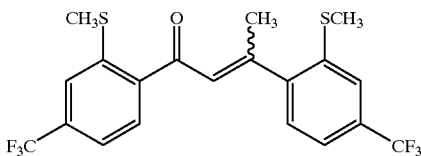

Example 1

Preparation of 1-Cyclopropyl-3-(2-thiomethyl-4-trifluoromethylphenyl)-1,3-propanedione (2):

2-Thiomethyl-4-trifluoromethylacetophenone (1; 97.1%; 6.03 g; 25.0 mmol) was dissolved in DMSO (12.5 mL). Methyl cyclopropanecarboxylate (7.5 mL; 75 mmol; 3 equiv) was added, and the resulting solution was cooled in an ice-water bath. Sodium methoxide (2.70 g; 50.0 mmol; 2.0 equiv) was added in one portion. The red reaction mixture was stirred in the ice-water bath for 5 min and the bath was removed. The reaction mixture was heated in a 40° C. oil bath for 8 h to consume all of the ketone 1 according to GC analysis. The heating was stopped and toluene (12.5 mL) was added. The reaction mixture was cooled in ice-water and 3 N HCl (20 mL; 60 mmol; 2.4 equiv) was added such that the temperature remained below 20° C. The mixture was diluted with pH 7 buffer (20 mL) and the layers were separated. The aqueous phase was extracted with an additional portion (12.5 mL) of toluene, and the combined extracts were washed with saturated aqueous sodium bicarbonate (10 mL), dried ($Na_2SO_4$) and concentrated to afford 7.63 g of crude 2. GC analysis using an internal standard indicated that the crude product was 81.8% 2 by weight, indicating an 83% yield for the condensation reaction.

The only by-products observed that were derived from ketone 1 were diketone 6 (2.7% by GC area percent) and enone 7 (2.6% by GC area percent). No detectable reduction products were observed.

2: $^1$H NMR ($CDCl_3$) enol δ 7.632 (d, 1H, J=7.68 Hz); 7.468 (s, 1H); 7.411 (dd, 1H, J=1.65, 7.97 Hz); 6.100 (s, 1H); 2.507 (s, 3H); 1.755 (m, 1H); 1.23 (m, 2H); 1.0 (m, 2H); keto δ 7.916 (1H, d, J=8.24 Hz); 7.535 (s, 1H); 4.237 (s, 2H); 2.491 (s, 3H). FDMS (m/e): 302 (M$^+$). GC (30 m DB-17, 100° C., 3 min; 100–280° C., 15°/min; 280° C., 10 min): $t_R$ 14.9 min.

Example 2

Preparation of 1-Cyclopropyl-3-(2-thiomethyl-4-trifluoromethylphenyl)-1,3-propanedione (2) with Ambient Temperature Addition:

2-Thiomethyl-4-trifluoromethylacetophenone (1; 97.1%; 6.03 g; 25.0 mmol) was dissolved in DMSO (12.5 mL). Methyl cyclopropanecarboxylate (MCPC) (7.5 mL; 75 mmol; 3 equiv) was added, and the resulting solution was stirred for 5 min at ambient temperature. Sodium methoxide (2.70 g; 50.0 mmol; 2.0 equiv) was added in one portion, resulting in a temperature increase of 9° C. (from 24° C. to 33° C.). The reaction mixture was allowed to cool back to ambient temperature and then heated in a 40° C. oil bath for 10 h to consume all of 1 according to GC analysis. The crude product was isolated as in Example 1 to afford 7.57 g of crude 2. Quantitative GC analysis using an internal standard indicated that the crude product contained 82.95% of 2 by weight, indicating an 83% yield of 2.

Example 3
Preparation of 1-Cyclopropyl-3-(2-thiomethyl-4-trifluoromethylphenyl)-1,3-propanedione (2) with Inverse Addition:

Methyl cyclopropanecarboxylate (MCPC) (7.5 mL; 75 mmol; 3 equiv) was dissolved in DMSO (6 mL) and sodium methoxide (2.70 g; 50.0 mmol; 2.0 equiv) was added. The resulting slurry was cooled to 5° C. and a solution of 2-thiomethyl-4-trifluoromethylacetophenone (1; 97.1%; 6.03 g; 25.0 mmol) in DMSO (6.5 mL) was added slowly dropwise via an addition funnel over 30 min. The funnel was rinsed with DMSO (1 mL), and the reaction mixture was stirred at 5° C. for 5 min and then heated in a 40° C. oil bath for 10 h to consume all of 1 according to GC analysis. The crude product was isolated as in Example 1 to afford 7.53 g of crude 2. Quantitative GC analysis using an internal standard indicated that the crude product contained 83.18% 2 by weight, indicating an 83% yield of 2.

Comparative Example 1
Preparation of Diketone 2 Using Sodium Methoxide in Toluene Toluene (70 g) and sodium methoxide (95%; 11.6 g; 0.20 mol; 2 equiv) were slurried together and heated to 65° C. 2-Thiomethyl-4-trifluoromethylacetophenone (1; 97.4%; 25.66 g; 0.10 mol) was dissolved in methyl cyclopropanecarboxylate (98%; 31 g; 0.31 mol; 3.1 equiv). This solution was added dropwise to the toluene/methoxide slurry over the course of a two hour period while maintaining the reaction temperature at 65° C. After the addition, the reaction mixture was held an additional two hours to consume all of 1 as determined by GC analysis. The reaction mixture was cooled to ambient conditions and quenched with conc. HCl (36%; 24.0 g; 0.24 mol; 2.4 equiv) and water (24 g). The aqueous layer was decanted and the organic layer was washed with water (30 g). The organic phase was concentrated under reduced pressure (25 mm Hg) at 50–55° C. This afforded 31.8 g of crude product which was assayed by GC internal standard to be 53.3% 2 by weight. This indicated a yield for this reaction of 52%. Predominant by-products were alcohol 3 and ester 4.

Comparative Example 2
Preparation of Diketone 2 in a Mixture of Toluene and DMSO Toluene (27.4 g), DMSO (27.4 g), methyl cyclopropanecarboxylate (20.0 g; 0.2 mol; 2.0 equiv) and 2-thiomethyl-4-trifluoromethylacetophenone (1; 99%; 23.6 g; 0.10 mol) were mixed together and stirred until a solution was obtained. The temperature was maintained at 20–30° C. while sodium methoxide (95%; 10.8 g; 0.19 mol; 1.9 equiv) was added. The temperature was adjusted to 40° C. and the reaction mixture was stirred for 6 h. The pH of the reaction mixture was adjusted to 5.5–6.0 with concentrated HCl (ca. 23 g) and water (75 g). Heptane (75 mL) was added and the mixture was stirred for 5 min. After settling for 5 min, the lower aqueous layer was decanted and the upper organic layer was washed with water (20 mL). The resulting organic solution was stripped under reduced pressure (25 mm Hg) at 50–55° C. to remove the solvent and afford 28.0 g of crude 2. Internal standard GC analysis determined the sample to be 78.0 wt % of 2, indicating a yield of 72%.

Example 4
Preparation of 1-Cyclopropyl-3-(2-thiomethyl-4-trifluoromethylphenyl)-1,3-propanedione (2):

Methyl 2-thiomethyl-4-trifluoromethylbenzoate (2.06 g; 8.23 mmol) was dissolved in DMSO (12.5 mL). Cyclopropyl methyl ketone (0.85 g; 10.1 mmol; 1.2 equiv) was added, and the resulting solution was cooled to 15° C. and sodium methoxide (0.62 g; 11.5 mmol; 1.4 equiv) was added in one portion. The reaction mixture was stirred for 5 min and then heated to 40° C. for 10 h. The reaction mixture was diluted with toluene (5 mL), cooled in ice-water, and 3 N HCl (5 mL) was added dropwise such that the temperature remained below 25° C. The layers were separated and the organic solution was washed with aqueous sodium bicarbonate (10 mL) and water (10 mL), dried with sodium sulfate, and concentrated to afford 1.83 g yield of crude 2. Quantitative GC analysis using an internal standard indicated that the crude product contained 98.4% 2 by weight, indicating a 72% yield of 2.

Example 5
Preparation of 1-Phenyl-3-cyclopropyl-1,3-propanedione (8):

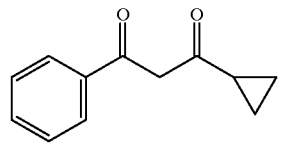

Acetophenone (10.1 g; 0.084 mol) and MCPC (25.2 g; 0.25 mol; 3 equiv) were dissolved in DMSO (46.1 g). Sodium methoxide (9.1 g; 0.168 mol; 2.0 equiv) was added slowly while maintaining the temperature below 30° C. The reaction mixture was then heated to 40° C. for 5 h. Heptane (100 mL) was added followed by sufficient 20% aqueous HCl such that the pH was less than 5. The mixture was stirred for 15 min and then allowed to settle. The lower aqueous layer was decanted and discarded. The upper organic layer was washed with 40 mL of water, and the solvent was stripped to afford 14 g of crude 8, which was 97.2% pure by GC (area %) to afford an 86% yield of 8.

Example 6
Preparation of 4-(2-Thiomethyl-4-trifluoromethylphenyl)-2,4-butanediol (9):

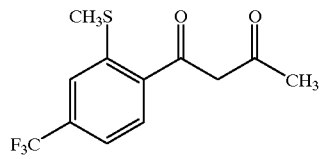

2-Thiomethyl-4-trifluoromethylacetophenone (1; 20 g; 0.085 mol) and methyl acetate (18.7 g; 0.25 mol; 3.0 equiv) were dissolved in DMSO (46.1 g). Sodium methoxide (9.1 g; 0.168 mol; 2.0 equiv) was added while maintaining the temperature below 30° C. The reaction mixture was then heated to 40° C. for 5 h. Heptane (100 mL) was added followed by sufficient 20% aqueous HCl such that the pH was less than 5. The mixture was stirred for 15 min and then allowed to settle. The lower aqueous layer was decanted and discarded. The upper organic layer was washed with 40 mL of water, and the solvent was stripped to afford 17.7 g of crude 9, which was 97.3% pure by GC (area %) to afford a 73% yield of 9.

Example 7
Preparation of 1,3-Dicyclopropyl-1,3-propanedione (10):

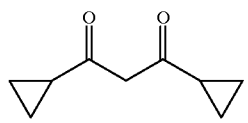

10

Cyclopropyl methyl ketone (10.8 g; 0.2 mol) and MCPC (40 mL; 0.4 mol; 2 equiv) were dissolved in DMSO (100 mL) and sodium methoxide (21.6 g; 0.4 mol; 2 equiv) was added. The resulting mixture was heated to 50–55° C. for 4–6 h and then cooled overnight to room temperature, The reaction mixture was quenched into 100 mL of 18% HCl. Water (50 mL) and toluene (50 mL) were added. The layers were thoroughly mixed and allowed to settle. The lower aqueous layer was removed and extracted with a second portion of toluene (25 mL). The combined toluene solution was washed with water (50 mL), dried with sodium sulfate, and concentrated. The residue was vacuum distilled to afford two fractions which were 92 and 99.5% pure 10, respectively.

Example 8
Preparation of 1,3-Dicyclopropyl-1,3-propanedione (10):

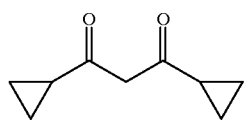

10

Cyclopropyl methyl ketone (2.5 mL; 25 mmol) was dissolved in DMSO (12.5 mL) and methyl cyclopropanecarboxylate (5.0 mL; 50 mmol; 2 equiv) was added. The reaction mixture was cooled in ice-water and sodium methoxide (2.70 g; 50 mmol; 2 equiv) was added. The reaction mixture was stirred for 5 min in the ice-water bath, the bath was removed, and the mixture was heated to 50–55° C. for 8 h. The reaction mixture was diluted with toluene (12.5 mL), cooled in ice-water, and 6 N HCl (9 mL) was added dropwise such that the temperature remained below 25 ° C. The layers were separated and the aqueous solution was extracted with additional toluene (10 mL). The combined organic solution was washed with aqueous sodium bicarbonate (10 mL), dried with sodium sulfate and concentrated to afford 3.50 g (92%) yield of 1,3-dicyclopropyl-1,3-propanedione.

$^1$H NMR (CDCl$_3$) enol δ 5.720 (s, 1H); 2.1–2.0 (m, 1H); 2.507 (s, 3H); 1.6–1.5 (m, 1H); 1.2–0.8 (m, 1H); keto δ 3.781 (s, 2H); 1.6–1.5 (m, 2H); 1.2–0.8 (m, 111).

Example 9
Preparation of Methyl 4,4-dimethyl-3-oxopentanoate (11):

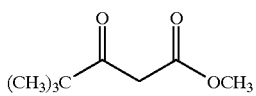

11

3,3-Dimethyl-2-butanone (10 g; 0.10 mol) was dissolved in DMSO (50 mL) and dimethyl carbonate (27 g; 0.30 mol; 3.0 equiv) was added. Sodium methoxide (10.8 g; 0.20 mol; 2.0 equiv) was added, resulting in a temperature rise to 30° C. The reaction mixture was heated to 40–50° C. for 4 h and then cooled to room temperature overnight. The reaction was quenched into a mixture of water (25 mL) and concentrated HCl (25 mL). Toluene (25 mL) was added and an additional 25 mL of water was added to dissolve salts. The layers were allowed to settle and the lower aqueous layer was removed and discarded. The organic layer was washed with water (25 mL), dried (Na$_2$SO$_4$), and filtered to afford 60 g of a toluene solution of 11. Analysis of this solution indicated 18.2 wt % of 11 to indicate a 69% yield.

The claimed invention is:

1. A process for preparing a 1,3-dicarbonyl compound comprising the step of reacting a ketone having an acidic proton at the α-position with an ester of the general formula (I):

(I)

where R and R' are, independently, a substituted or unsubstituted C$_1$–C$_{10}$ alkyl, C$_3$–C$_8$ cycloalkyl, heterocycloalkyl, aryl or heteroaryl group in the presence of an alkoxide base in DMSO as the sole solvent.

2. A process of claim 1, wherein the molar ratio of said ester to said ketone is about 0.8–6.0:1.0.

3. A process of claim 1, wherein said alkoxide base is an alkali metal alkoxide or an ammonium alkoxide.

4. A process of claim 3, wherein said alkoxide base is an alkali metal alkoxide.

5. A process of claim 4, wherein said alkali metal alkoxide is sodium methoxide.

6. A process of claim 3, wherein the molar ratio of said alkali metal alkoxide to said ketone is about 1.5–3.0:1.0.

7. A process of claim 6, wherein said molar ratio is 2.0:1.0.

8. A process of claim 1, wherein said ketone is a methyl ketone.

9. A process of claim 8, wherein said methyl ketone is selected from the group consisting of acetophenone, 2-thiomethyl-4-trifluoromethyl-acetophenone, cyclopropyl methyl ketone, and 3,3-dimethyl-2-butanone.

10. A process for preparing a 1,3-dicarbonyl compound comprising the step of reacting a ketone having an acidic proton at the α-position with a carbonate of the general formula (II):

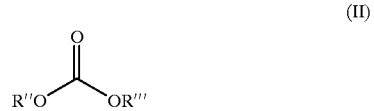

(II)

where R" and R'" are, independently, a substituted or unsubstituted C$_1$–C$_{10}$ alkyl, C$_3$–C$_8$ cycloalkyl, heterocycloalkyl, aromatic or heteroaromatic group in the presence of an alkoxide base in DMSO as the sole solvent.

11. A process of claim 10, wherein the molar ratio of said carbonate to said ketone is about 1.5–6.0:1.0.

12. A process of claim 10, wherein said alkoxide base is an alkali metal alkoxide or an ammonium alkoxide.

13. A process of claim 12, wherein said alkoxide base is an alkali metal alkoxide.

14. A process of claim 13, wherein said alkali metal alkoxide is sodium methoxide.

15. A process of claim 13, wherein the molar ratio of said alkali metal alkoxide to said ketone is 1.5–3.0:1.0.

16. A process of claim 15, wherein said molar ratio is 2.0:1.0.

17. A process of claim 10, wherein said ketone is a methyl ketone.

18. A process of claim 17, wherein said methyl ketone is selected from the group consisting of acetophenone, 2-thiomethyl-4-trifluoromethyl-acetophenone, cyclopropyl methyl ketone, and 3,3-dimethyl-2-butanone.

19. A process of claim 11, wherein said R" and R'" of said carbonate are, independently, a $C_1$–$C_5$ alkyl group.

20. A process of claim 19, wherein said R" and R'" of said carbonate are each a methyl group.

21. A process of claim 18, wherein said methyl ketone is cyclopropyl methyl ketone and said carbonate is dimethyl carbonate.

* * * * *